United States Patent [19]

Bruce et al.

[11] Patent Number: 4,612,805
[45] Date of Patent: Sep. 23, 1986

[54] ADHESION CHARACTERIZATION TEST SITE

[75] Inventors: James A. Bruce, Underhill; Rajesh G. Narechania, Essex Junction, both of Vt.

[73] Assignee: International Business Machines Corporation, Armonk, N.Y.

[21] Appl. No.: 685,867

[22] Filed: Dec. 24, 1984

[51] Int. Cl.[4] .................. G01B 21/08; G01N 3/08; G01N 19/04
[52] U.S. Cl. .................................. 73/150 A; 73/842
[58] Field of Search ................... 73/150 A, 827, 842

[56] References Cited

U.S. PATENT DOCUMENTS

| | | | |
|---|---|---|---|
| 3,580,065 | 5/1971 | Strittmater | 73/150 A |
| 3,985,597 | 10/1976 | Zielinski | 357/71 |
| 4,024,567 | 5/1977 | Iwata et al. | 357/71 |
| 4,316,200 | 2/1982 | Ames et al. | 357/71 |
| 4,365,264 | 12/1982 | Mukai et al. | 357/73 |
| 4,367,119 | 1/1983 | Logan et al. | 357/71 |
| 4,501,154 | 2/1985 | Mori | 73/827 |
| 4,533,935 | 8/1985 | Mochizuki | 357/71 |

FOREIGN PATENT DOCUMENTS 146210 1/1981 Fed. Rep. of Germany ... 73/150 A

OTHER PUBLICATIONS

C. Altman et al., "Measuring Adhesion of Thin Films", *IBM Tech. Disclosure Bulletin*, vol. 12, No. 10, Mar. 1970, p. 1674.

Chang, "Testing Site for Determining Capacitances of Integrated Circuits", *IBM Tech. Disclosure Bulletin*, vol. 16, No. 6, Nov. 1973, pp. 1990-1992.

Lukianoff, "Testsite Layout", *IBM Tech. Disclosure Bulletin*, vol. 24, No. 12, May 1982, pp. 6445-6447.

*Primary Examiner*—Charles Frankfort
*Assistant Examiner*—W. Morris Worth
*Attorney, Agent, or Firm*—Mark F. Chadurjian

[57] ABSTRACT

A test site for gauging the adhesion between the insulating layers and the metal layers used to produce the various devices on a semiconductor chip. The chip-sized test site can be formed along with the product chips on the product wafers. The layers of the test site are arranged such that a first polyimide layer forms a first test interface with a silicon nitride layer and a second test interface with a first metal layer, and a second polyimide layer forms a third test interface with a second metal layer, a fourth test interface with the first polyimide layer, and a fifth test interface with the silicon nitride layer. These five interfaces form a single continuous adhesion test interface. During a 90° peel test, the layers of the test site will sequentially separate along this interface. Thus, the adhesion at five different interfaces can be tested during a single peel test on a chip-sized test site.

22 Claims, 3 Drawing Figures

ADHESION CHARACTERIZATION TEST SITE

BACKGROUND OF THE INVENTION

1. Technical Field

The present invention relates to a test site for determining the adhesive characteristics of the various materials used in processing a semiconductor chip.

2. Background Art

During the course of the processing of semiconductor chips, a plurality of insulative, metallizing and passivating layers are deposited on the surface of a semiconductor substrate to form the various devices on each chip. These various layers must exhibit some degree of adhesion to one another. If this interlayer adhesion is insufficient, moisture or other impurities can penetrate the seams between layers, causing corrosion or other impurity-induced phenomena which adversely affect the performance of the resulting chip.

Accordingly, various methods have been developed for testing the adhesion between layers used to form a semiconductor device. An article by C. Altman et al ("Measuring Adhesion of Thin Films", *IBM Technical Disclosure Bulletin*, Vol. 12, No. 10, March 1970, p. 1674) discloses a method of measuring the adhesion between a film and a substrate, in which a testor is bonded to the film and an upward force is imparted thereto to pull the film away from the substrate. A more common testing method (commonly referred to as a "peel test") involves cleaving a film to expose the seam between the film and the substrate and "peeling" the film away from the substrate. In a "90° peel test", the angle between the peeled film and the film remaining on the substrate is approximately 90°.

Heretofore, this peel test has been performed on a single layer test structure. For example, a semiconductor wafer having a silicon nitride coating is covered with eight strips of insulative material. By performing a peel test on each strip of the wafer, eight interfaces per wafer can be tested.

It has been found that test wafers constructed in the manner described above are inefficient when used to monitor wafer lot processes. One disadvantage is that only eight interfaces are tested on each test wafer. Another disadvantage is that each test wafer only tests one type of interface; for example, if insulator-metal and insulator-insulator interfaces were to be tested, two different test wafers would have to be produced.

SUMMARY OF THE INVENTION

Accordingly, it is an object of the present invention to produce an improved test structure for determining the adhesion between layers used in a semiconductor manufacturing process.

It is another object of the present invention to produce a test site which can be used to monitor a plurality of interfaces during a single peel test.

It is yet another object of the present invention to produce a multi-layer test site which is the same size as the product chip.

The above and other objects of the invention are realized by an Extended Adhesion Characterization Test Site ("EXACTS") which provides for adhesion characterization between the insulator layers and the remaining layers (as well as between the insulator layers) used to form multi-layered semiconductive devices. The test site has a semiconductive substrate which is covered by a silicon nitride layer. A first metal layer is formed on the nitride layer, and a first insulator layer is formed on the nitride layer and a portion of the first metal layer, forming first and second test interfaces therewith, respectively. A second metal layer is formed on the first metal layer and the first insulator layer, and a second insulator layer is coated over the entire device. The second insulator layer forms a third test interface with the first insulator layer, and a fourth test interface with the second metal layer. During a 90° peel test, the two insulator layers are peeled away from the underlying layers along the above-described four test interfaces. Thus, the strength of the adhesions between a plurality of layers can be determined by the use of a single test site which is the same size as a product chip.

BRIEF DESCRIPTION OF THE DRAWING

The foregoing and other structures and teachings of the invention will become more apparent upon a description of the best mode for carrying out the present invention. In the description to follow, reference will be made to the accompanying drawing, in which.

BEST MODE FOR CARRYING OUT THE INVENTION

Figure 1:
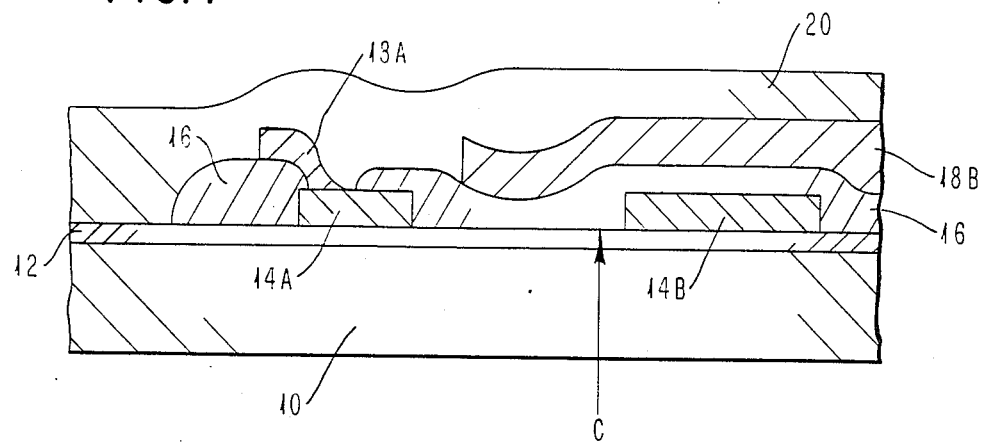
FIG. 1 is a cross-sectional view of the test site of the invention.

FIG. 1 (not to scale) presents a cross-sectional view of one embodiment of the test site of the invention. Note that this cross-sectional view is not drawn to scale. A layer of silicon nitride 12 is formed on a semiconductive wafer 10 using typical techniques. An aluminum layer 14 is formed on the silicon nitride layer 12 by deposition or other techniques. Note that aluminum is given by way of example; that is, metal layer 14 could be made of other metals or alloys which have adhesion characteristics as will be discussed in more detail below. Metal layer 14 is patterned (by etching through a mask) to form test regions 14A and support regions 14B. Note that support regions 14B of the first metal layer are not used during the adhesion test.

Metal layer 14 is then covered by a first insulator layer 16. Insulator layer 16 comprises any one of a number of known insulative materials, such as polyimide. The first insulator layer is patterned so that a portion of the upper surface of test region 14A of metal layer 14 is exposed. In addition, the first insulator layer 16 is etched so that a portion of the silicon nitride layer 12 is also exposed.

A second aluminum layer 18 is then formed on the upper surface of the first insulator layer 16. Similarly to the first metal layer, the second metal layer 18 is patterned to form test regions 18A and support regions 18B. As shown in FIG. 1, test region 18A of metal layer 18 partially covers the exposed portion of the first metal layer test region 14A. Finally, a second insulator layer 20 (e.g., a passivation layer composed of an insulator such as polyimide) is coated over the entire test site. Note that the portion of the silicon nitride layer 12 which remained exposed after the deposition of the first insulator layer 16 is now covered by the second insulator layer 20. In addition, note that the second insulator layer 20 covers a portion of the first insulator layer 16 which remained exposed after the formation of the second metal layer test region 18A. Finally, note that the passivation layer 20 covers the remainder of the exposed surface of the first metal layer test region 14A which was not covered by the second metal layer test region 18A.

The test site as described above can be formed during back end of line (BEOL) processing of the product wafers. In other words, the specific layers as described above are the same as those used in forming the product chips. Thus, the test site of the invention can be formed concurrently with the product chips on the same wafer. In addition, since the test site is the same size as the chips, approximately 140 test sites can be produced on one wafer.

Figure 2:
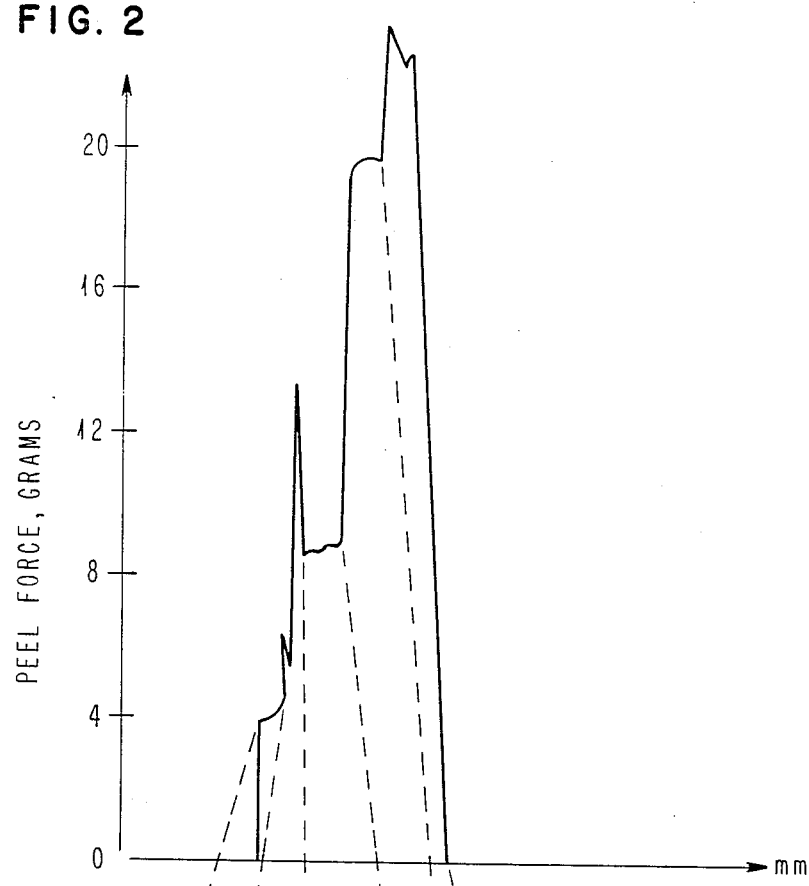
FIG. 2 is a graph showing the adhesive strength of the layers along an adhesion test path as shown in FIG. 1.
Figure 2:
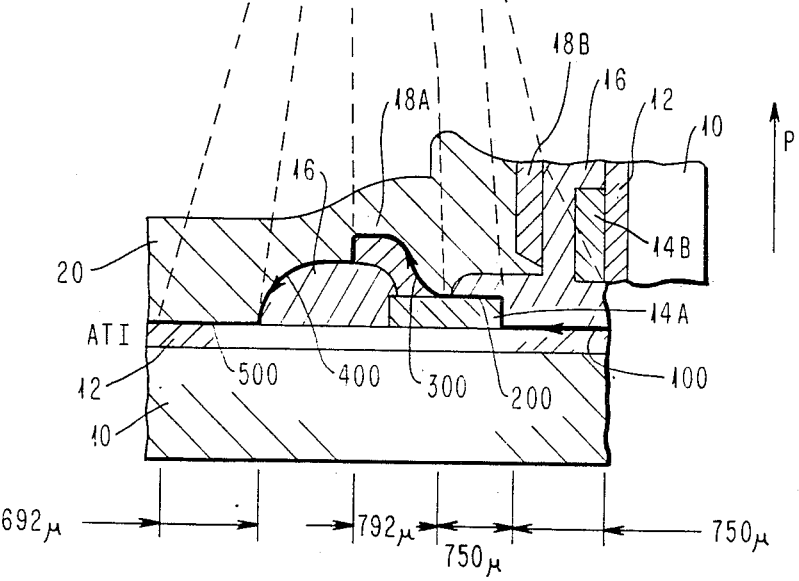

The operation of the test site of the invention will now be described with reference to FIG. 2. Note that this figure is not drawn to scale. In general, a conventional 90° peel test is conducted on the test site, using equipment such as the Instron material testing system marketed by the Instron Corporation of Massachusetts. The test site is cleaved along line C in FIG. 1. A force approximately orthogonal to the plane of substate 10 is then applied by the peel test equipment to the cleaved ends of the layers (as signified by arrow P in FIG. 2). The force resisting peel (i.e. the adhesion between layers) is determined by a transducer which provides an electrical signal representative of the force expended during peel. This signal is sent to a display such as a CRT screen or a chart recorder. The display produces a graph of peel resistance force versus distance, as shown in FIG. 2.

The test site of the invention is used to test the adhesion at discrete layer interfaces (hereinafter referred to as "test interfaces"). The layers are configured (i.e. etched) such that each test interface is of a length (ranging from approximately 200 to 800 μm) sufficient to provide a discrete force reading. Note that in FIG. 2, test interface 100 is the interface between the silicon nitride layer 12 and the first insulator layer 16. Test interface 200 is the interface between the first metal layer test portion 14A and the first insulator layer 16. Test interface 300 is the interface between the second metal layer test portion 18A and the second insulator layer 20. Test interface 400 is the interface between the first insulator layer 16 and the second insulator layer 20. Finally, test interface 500 is the interface between silicon nitride layer 12 and the second insulator layer 20. The layers of the test site sequentially separate along test interfaces 100-500. Thus, the interfaces collectively form a single continuous adhesion test interface (hereinafter referred to as the "ATI").

Several factors insure that the layers of the test site will separate along the ATI. One factor is the respective adhesions between the layers. That is, the composition of the layers is preselected such that separation will occur along the ATI. For example, the composition of metal layer 14 (e.g. aluminum) is selected such that the layers will separate along test interface 200 rather than separating between metal layer 14 and nitride layer 12. Similarly, the composition of metal layer 18 is preselected such that the layers will separate along test interface 300 rather than separating between second metal layer 18 and first insulator layer 16. In addition to aluminum, the inventors have noted that alloys of aluminum (e.g. 95% Al, 5% Cu; 94% Al, 5% Cu, 1% Si; 85% Al, 10% Ti, 5% Cu); refractory metals such as tungsten, titanium or molybdenum; and any other metallizations in which the metal is fused during processing to an underlying layer, can be used in the invention.

Another factor determining layer separation is the specific placement of the layers. That is, when the respective layers are arranged in the manner as shown in FIGS. 1 and 2, the resulting ATI provides adhesion characterization between the insulative layers (layers 16 and 20) and each of the remaining layers (layers 12, 14A and 18A), as well as between insulator layers (layers 16 and 20) used to form a product chip.

Finally, a third factor is the composition of the first and second insulator layers. At all times, these layers must have a stress/strain characteristic such that they will not cleave as they are being peeled away from the wafer. The inventors have noted that any sort of organic resin insulator (e.g. polyimide) provides these characteristics.

When the peel test is initiated, the test site is cleaved along line C to expose the start of the ATI such that the layers will separate along the first test interface 100 when an upward peel force P is applied to the cleaved layers. As shown in FIG. 2, the adhesion between these two layers is relatively high (i.e. approximately 22-23 grams/mm). When the first insulator layer has been completely separated from silicon nitride layer 12 along test interface 100, the first insulator layer 16 separates from the first metal layer test portion 14A along test interface 200, and a lower peel resistive force (i.e. approximately 19-20 grams/mm) is observed. This process continues until all of the layers separate along the ATI.

Figure 3:
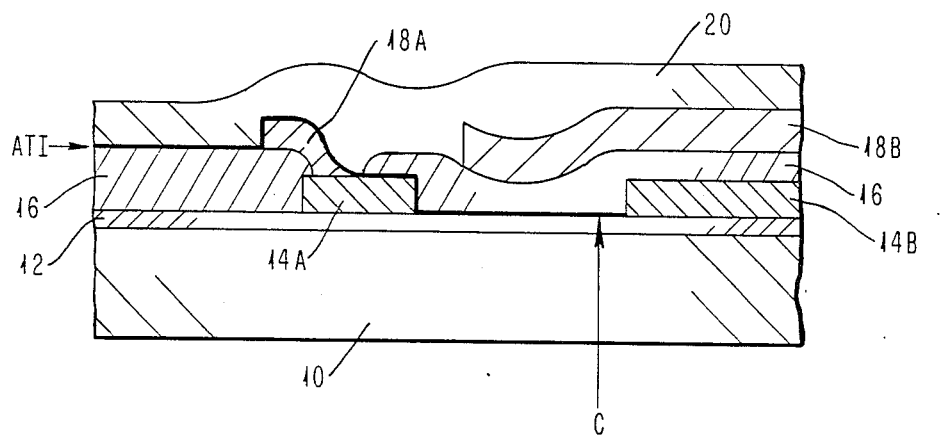
FIG. 3 is a cross-sectional view of another embodiment of the test site of the invention.

FIG. 3 is a cross-sectional view of another embodiment of the invention. Again, note that this cross-sectional view is not drawn to scale. As shown in FIG. 3, layer 16 is extended so that the second insulator 20 does not form a fifth test interface 500 with silicon nitride layer 12. That is, the ATI is made up of test interfaces 100-400 as described above.

Thus, as described above, the test site of the invention can be used to provide measurements of the adhesions between preselected ones of the layers used to manufacture the product chips. A feature of the invention is that since the test site is the same size as the product chips and is formed by the same layers used to produce the various devices on the product chip, the test site can be formed on a product wafer. Thus, the test site can be used to monitor lot-to-lot and wafer-to-wafer variations, to more accurately track the line process.

It is re-emphasized that the particular compositions of the layers as disclosed above are given by way of example. That is, any sort of metal or insulator can be substituted for the metals/insulators disclosed, so long as they meet the above-described adhesion/stress-strain criteria, respectively.

It is to be understood that modifications can be made to the structures and teachings of the best mode as described above without departing from the spirit and scope of the present invention.

We claim:

1. A test site for gauging degrees of adhesion between respective layers used in forming a multi-layered semiconductor chip, comprising:
   a first insulator layer overlaying a semiconductive substrate;
   a first patterned conductive layer overlaying said first insulator layer;
   a second insulator layer overlaying portions of said first patterned conductive layer, and forming a first test interface with said first insulator layer and a second test interface with said portions of said first patterned conductive layer, respectively;

a second patterned conductive layer overlaying a portion of said second insulator layer; and a third insulator layer overlaying said second patterned conductive layer and a portion of said second insulator layer, and forming third and fourth test interfaces therewith, respectively;

said first, second, third and fourth respective test interfaces being arranged in an end to end pattern to form a single continuous adhesion test interface, the layers of said test site sequentially separating along said single continuous adhesion test interface so as to provide a characterization of the degrees of adhesion at each of said respective first, second, third, and fourth test interfaces during the course of a single adhesion peel test.

2. The test site as recited in claim 1, wherein said first and second patterned conductive layers are comprised of a metal.

3. The test site as recited in claim 2, wherein said metal is selected from the group consisting of aluminum, aluminum alloys and refractory metals.

4. The test site as recited in claim 1, wherein said second and third insulator layers are comprised of an organic resin.

5. The test site as recited in claim 4, wherein said first insulator layer comprises silicon nitride and said second and third insulator layers comprise polyimide.

6. The test site as recited in claim 1, wherein the degree of adhesion between said first patterned conductive layer and said first insulator layer is greater than the degree of adhesion between said second insulator layer and said first patterned conductive layer, and the degree of adhesion between said second patterned conductive layer and said first patterned conductive layer is greater than the degree of adhesion between said third insulator layer and said second patterned conductive layer.

7. The test site as recited in claim 1, wherein said test site is of a size approximately the same as that of the multi-layered semiconductor chip.

8. The test site as recited in claim 7, wherein said test site and the multi-layered semiconductive chip are formed on the same wafer.

9. A multi-layered test site for determining adhesive characteristics of layers used to form various devices of a product chip formed on a wafer, the test site being of a size approximately the same as that of the product chip and being formed on the same wafer as the product chip, said test site comprising:

a first insulator layer overlaying the wafer;

a first patterned metal layer overlaying a portion of said first insulator layer;

a second insulator layer overlaying a portion of said first patterned metal layer and a portion of said first insulator layer, said second insulator layer forming a first test interface with said portion of said first insulator layer and a second test interface with said portion of said first patterned metal layer;

a second patterned metal layer overlaying a portion of said second insulator layer and a portion of said first patterned metal layer; and a passivation layer overlaying said second patterned metal layer, a portion of said first patterned metal layer, a portion of said second insulator layer, and a portion of said first insulator layer, said passivation layer forming a third test interface with said portion of said second patterned metal layer, a fourth test interface with said portion of said second insulator layer, and a fifth test interface with said portion of said first insulator layer;

said first, second, third, fourth and fifth test interfaces being arranged in an end to end pattern to form a single continuous adhesion test interface;

the layers of the multi-layered test site separating along said single adhesion test interface to provide a characterization of adhesion between the layers at said first, second, third, fourth and fifth test interfaces, respectively, during the course of a single adhesion peel test.

10. The test site as recited in claim 9, wherein said insulator layer and said passivation layer are comprised of organic resins.

11. The test site as recited in claim 9, wherein said first and second metal layers are comprised of aluminum.

12. The test site as recited in claim 9, wherein said first and second metal layers are comprised of an aluminum alloy.

13. The test site as recited in claim 12, wherein said alluminum alloy is selected from the group consisting of an aluminum-copper alloy, an aluminum-copper-silicon alloy, and an aluminum-titanium-copper alloy.

14. The test site as recited in claim 9, wherein said first and second metal layers are comprised of a refractory metal.

15. A test site for gauging degrees of adhesion between various layers which are used in forming a multi-layered semiconductive device, comprising:

a layer of silicon nitride overlaying a semiconductive substrate;

a first conductive layer overlaying portions of said silicon nitride layer;

a first insulator layer overlaying portions of said silicon nitride layer and said first conductive layer, said first conductive layer having a greater adhesion to said silicon nitride layer than said first insulator layer has to said first conductive layer, said first insulator layer thus forming a first test interface with said silicon nitride layer and a second test interface with said first conductive layer;

a second conductive layer overlaying a portion of said first conductive layer;

a second insulator layer overlaying at least said first insulator layer and said second conductive layer, said second conductive layer having a greater adhesion to said first conductive layer than said second insulator layer has to said second conductive layer, said second insulator layer thus forming a third test interface with said second conductive layer and a fourth test interface with said first insulator layer;

said first, second, third and fourth respective test interfaces being arranged in an end to end pattern to form a single continuous adhesion test interface, said layers of said test site separating along said single adhesion test interface during a single adhesion peel test to provide characterization of the degree of adhesions at each of said first, second, third, and fourth respective test interfaces.

16. A method of determining degrees of adhesion between respective insulative and non-insulative layers, and among the respective insulative layers, utilized in forming a semiconductive device, comprising the steps of:
- depositing and patterning said insulative and non-insulative layers on a substrate to form a test site, said layers being configured such that each of said non-insulative layers forms a test interface with at least one of said insulative layers, and such that at least one of said insulative layers overlays another of said insulative layers to form a test interface therewith, said test interfaces being arranged in an end to end pattern to form a single continuous adhesion test interface;
- cleaving said test site to expose one end of said single continuous adhesion test interface;
- applying a peel force to the layers of said test site overlaying said exposed end of said single continuous test interface, so that the layers of the test site separate along said single continuous adhesion test interface; and
- monitoring the force expended in separating the layers of the test site.

17. The method as recited in claim 16 wherein at least two of said insulative layers are comprised of an organic resin.

18. The method as recited in claim 17 wherein said organic resin comprises polyimide.

19. The method as recited in claim 16 wherein at least one of said insulative layers is comprised of silicon nitride.

20. The method as recited in claim 16 wherein at least one of said non-insulative layers is comprised of a metal.

21. The method as recited in claim 20 wherein said metal is selected from the group consisting of aluminum, aluminum alloys and refractory metals.

22. A method of determining degrees of adhesion between insulative layers and conductive layers, and between insulative layers, which are used to form various devices on a product chip, comprising the steps of:
- depositing and patterning said layers on a semiconductive wafer to form a test site thereon, said test site being of a size approximately the same as that of the product chip, said layers being configured such that each of said conductive layers forms a test interface with at least one of said insulative layers, and at least one of said insulative layers overlays another of said insulative layers to form a test interface therewith, said test interfaces being arranged in an end to end pattern to form a single continuous adhesion test interface;
- cleaving said test site to a point where one end of said single continuous adhesion test interface is exposed;
- applying a peel force to the layers of said test site overlaying said exposed end, the adhesions between the layers being such that said layers separate along said single continuous adhesion test interface; and
- producing an electrical signal indicative of the force resisting said peel force, whereby the degree of adhesion between respective ones of a plurality of layers defining said single continuous adhesion test interface can be determined during the course of a single peel test.

* * * * *